United States Patent [19]

Krämer et al.

[11] 4,406,909
[45] Sep. 27, 1983

[54] COMBATING FUNGI WITH 4-SUBSTITUTED 1-AZOLYL-1-PHENOXY-3,3-DIMETHYL-BUTAN-2-ONES AND -OLS

[75] Inventors: Wolfgang Krämer; Hans-Ludwig Elbe, both of Wuppertal; Karl H. Büchel, Burscheid; Wilhelm Brandes, Leichlingen; Paul-Ernst Frohberger, Leverkusen, all of Fed. Rep. of Germany

[73] Assignee: Bayer Aktiengesellschaft, Leverkusen, Fed. Rep. of Germany

[21] Appl. No.: 265,050

[22] Filed: May 19, 1981

[30] Foreign Application Priority Data

Jun. 7, 1980 [DE] Fed. Rep. of Germany ....... 3021551

[51] Int. Cl.$^3$ .................... A01N 43/50; A01N 43/64; C07D 233/60; C07D 249/08
[52] U.S. Cl. ................................. 424/269; 424/245; 424/273 R; 548/101; 548/262; 548/341; 260/456 P; 260/465 F; 260/465.7; 560/11; 560/18; 560/53; 568/308; 568/325; 568/414; 568/419
[58] Field of Search ....................... 548/262, 101, 341; 424/269, 245, 273 R

[56] References Cited

U.S. PATENT DOCUMENTS

| | | | |
|---|---|---|---|
| 3,912,752 | 10/1975 | Meiser et al. | 424/269 |
| 4,154,842 | 5/1979 | Krämer et al. | 424/273 R |
| 4,215,127 | 7/1980 | Rogers et al. | 548/262 |
| 4,229,459 | 10/1980 | Krämer et al. | 424/269 |
| 4,255,434 | 3/1981 | Krämer et al. | 548/262 |

FOREIGN PATENT DOCUMENTS

| | | | |
|---|---|---|---|
| 4303 | 10/1979 | European Pat. Off. | 424/269 |
| 2635663 | 2/1978 | Fed. Rep. of Germany | 548/262 |
| 2635664 | 2/1978 | Fed. Rep. of Germany | 548/262 |
| 2635665 | 2/1978 | Fed. Rep. of Germany | 548/262 |
| 2635666 | 2/1978 | Fed. Rep. of Germany | 548/262 |
| 2720868 | 11/1978 | Fed. Rep. of Germany | 548/262 |
| 2811916 | 9/1979 | Fed. Rep. of Germany | 424/269 |

Primary Examiner—Alton D. Rollins
Attorney, Agent, or Firm—Sprung, Horn, Kramer & Woods

[57] ABSTRACT

A fungicidally active 4-substituted-1-azolyl-1-phenoxy-3,3-dimethyl-butan-2-one or -ol of the formula

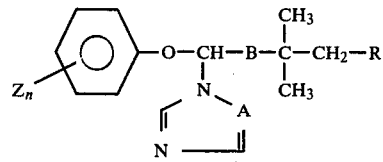

in which A is a nitrogen atom or CH,
B is —CO— or CH(OH),
R is cyano or X—R$^1$,
R$^1$ is alkyl, optionally substituted aryl or optionally substituted aralkyl,
X is oxygen, sulphur, SO or SO$_2$,
Z each independently is halogen, alkyl, halogenoalkyl, alkoxy, alkylthio, alkylsulphonyl, nitro, cyano, alkoxycarbonyl or optionally substituted phenyl, and
n is 0, 1, 2 or 3, or an addition product thereof with a physiologically acceptable acid or with a metal salt. Intermediates therefor of the formula

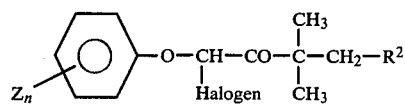

and

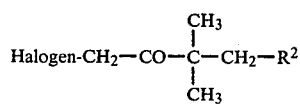

are also new.

9 Claims, No Drawings

COMBATING FUNGI WITH 4-SUBSTITUTED 1-AZOLYL-1-PHENOXY-3,3-DIMETHYL-BUTAN-2-ONES AND -OLS

The present invention relates to certain new 4-substituted 1-azolyl-1-phenoxy-3,3-dimethyl-butan-2-ones and -ols, to a process for their preparation and to their use as fungicides.

It has already been disclosed that, in general azolylalkyl derivatives, for example 1-hydroxyethyl-triazole derivatives, and, in particular, triazolyl and imidazolyl ether-ketones and -carbinols have good fungicidal properties (see U.S. Pat. No. 3,912,752, issued Oct. 14, 1975 and continuation-in-part U.S. Pat. No. 4,147,791, issued Apr. 3, 1979; U.S. Pat. No. 3,952,002, issued Apr. 20, 1976; U.S. Ser. No. 792,756, filed May 2, 1977; U.S. Ser. No. 964,215, filed Nov. 27, 1978, now U.S. Pat. No. 4,255,434; U.S. Pat. No. 4,154,842, issued May 15, 1979 and German Patent Specification DE-OS No. 2,632,602). However, the action of these compounds is not always completely satisfactory, especially when small amounts and low concentrations are applied.

The present invention now provides, as new compounds, the 4-substituted 1-azolyl-1-phenoxy-3,3-dimethyl-butan-2-ones and -ols of the general formula

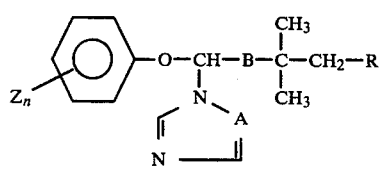

in which
A represents a nitrogen atom or the CH group,
B represents the keto group or the CH(OH) group,
R represents cyano or the grouping $X-R^1$,
wherein
$R^1$ represents alkyl, optionally substituted aryl or optionally substituted aralkyl, and
X represents oxygen, sulphur or the SO or $SO_2$ group,
Z represents halogen, alkyl, halogenoalkyl, alkoxy, alkylthio, alkylsulphonyl, nitro, cyano, alkoxycarbonyl or optionally substituted phenyl and
n represents 0, 1, 2 or 3, each Z being selected independently when n is 2 or 3,
and physiologically acceptable acid addition salts and metal salt complexes thereof.

Those compounds of the formula (I) in which B represents the CH(OH) group have two asymmetric carbon atoms; they can therefore exist in the form of two geometric isomers (threo-form and erythro-form), which can be obtained in various proportions. In both cases, they are in the form of optical isomers. All the isomers are embraced by formula (I) above.

The invention also provides a process for the preparation of a 4-substituted 1-azolyl-1-phenoxy-3,3-dimethyl-butan-2-one or -ol of the formula (I) in which (a) a halogenoether-ketone of the general formula

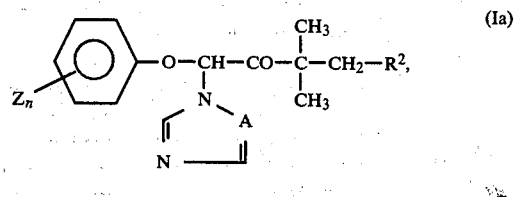

in which
Z and n have the abovementioned meanings,
Hal represents halogen (preferably chlorine or bromine), and
$R^2$ represents $X^1-R^1$ or cyano,
wherein
$X^1$ represents oxygen or sulphur and
$R^1$ has the abovementioned meaning,
is reacted with an azole of the general formula

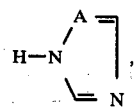

in which
A has the abovementioned meaning, if appropriate in the presence of a diluent and in the presence of an acid-binding agent, or (b) a keto derivative of the general formula

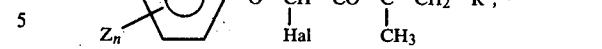

in which
A, $R^2$, Z and n have the abovementioned meanings, is reduced (the reduction may be effected in the customary manner by any known method) or (c) a thio derivative of the general formula

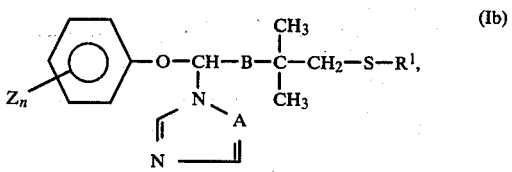

in which A, B, Z, $R^1$ and n have the abovementioned meanings, is oxidized (the oxidation may be effected by any known method in the customary manner).

If appropriate, an acid or a metal salt can then be added onto a compound of the formula (I) thus obtained. In some cases, it proves advantageous to obtain a compound of the formula (I) in a pure form via a salt thereof.

The 4-substituted 1-azolyl-1-phenoxy-3,3-dimethyl-butan-2-ones and -ols of this invention have powerful fungicidal properties. Surprisingly, the compounds according to the invention exhibit a considerably more powerful action than the azolyl-alkyl derivatives which are known from the state of the art and are closely related compounds chemically and/or from the point of view of their action. The substances according to the invention thus represent an enrichment of the art.

The formula (I) provides a general definition of the 4-substituted 1-azolyl-1-phenoxy-3,3-dimethyl-butan-2-ones and -ols according to the invention. Preferably, in this formula, R represents cyano or the grouping X—$R^1$, $R^1$ represents straight-chain or branched alkyl with 1 to 6 carbon atoms, or optionally substituted aryl with 6 to 10 carbon atoms or optionally substituted aralkyl with 6 to 10 carbon atoms in the aryl part and 1 to 2 carbon atoms in the alkyl part, each substituent preferably being selected from halogen, cyano, nitro, alkoxycarbonyl with 1 to 4 carbon atoms in the alkyl part, alkyl and alkoxy with in either case 1 to 4 carbon atoms, dialkylamino with 1 to 2 carbon atoms in each alkyl part and phenyl which is optionally substituted by halogen, and Z represents halogen, straight-chain or branched alkyl or alkoxy with in either case 1 to 4 carbon atoms, halogenoalkyl with 1 to 2 carbon atoms and 1 to 5 identical or different halogen atoms (especially fluorine and chlorine atoms), alkylthio with 1 to 4 carbon atoms, alkylsulphonyl with 1 to 4 carbon atoms, nitro, cyano, alkoxycarbonyl with 1 to 4 carbon atoms in the alkyl part or phenyl which is optionally substituted by halogen.

Particularly preferred compounds of the formula (I) are those in which R represents cyano or the grouping X—$R^1$, $R^1$ represents straight-chain or branched alkyl with 1 to 4 carbon atoms or optionally substituted phenyl or benzyl, each substituent being selected from fluorine, chlorine, bromine, cyano, nitro, methoxycarbonyl, methyl, ethyl, isopropyl, tert.-butyl, methoxy, dimethylamino and phenyl which is optionally substituted by fluorine or chlorine; Z represents fluorine, chlorine, bromine, iodine, methyl, ethyl, isopropyl, tert.-butyl, methoxy, nitro, cyano, methoxycarbonyl, ethoxycarbonyl, methylthio, methylsulphonyl, trifluoromethyl or phenyl which is optionally substituted by fluorine or chlorine; and n represents 0, 1 or 2.

The following compounds of the general formula (I) may be mentioned specifically, in addition to the compounds mentioned later in the preparative examples:

TABLE 1

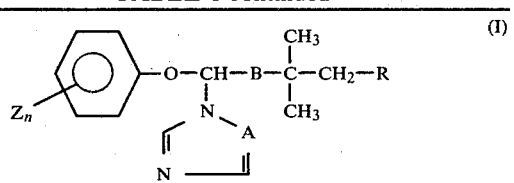

(I)

| $Z_n$ | A | B | R |
|---|---|---|---|
| 4-Cl | CH | CO | —S—⟨phenyl⟩ |
| 4-Cl | CH | CO | —SO₂—⟨phenyl⟩ |
| 4-Cl | CH | CO | —S—⟨phenyl⟩—Cl |
| 4-Cl | CH | CO | —SO₂—⟨phenyl⟩—Cl |
| 4-Cl | CH | CH(OH) | —S—⟨phenyl⟩ |
| 4-Cl | CH | CH(OH) | —SO₂—⟨phenyl⟩ |
| 4-Cl | CH | CH(OH) | —S—⟨phenyl⟩—Cl |
| 4-Cl | CH | CH(OH) | —SO₂—⟨phenyl⟩—Cl |
| 4-CN | N | CO | —O—⟨2,4-diCl-phenyl⟩ |
| 4-CN | CH | CO | —O—⟨2,4-diCl-phenyl⟩ |
| 4-CN | N | CH(OH) | —O—⟨2,4-diCl-phenyl⟩ |
| 4-CN | CH | CH(OH) | —O—⟨2,4-diCl-phenyl⟩ |
| 4-COOCH₃ | N | CO | —O—⟨phenyl⟩—Cl, CH₃ |
| 4-COOCH₃ | CH | CO | —O—⟨phenyl⟩—Cl, CH₃ |
| 4-COOCH₃ | N | CH(OH) | —O—⟨phenyl⟩—Cl, CH₃ |
| 4-COOCH₃ | CH | CH(OH) | —O—⟨phenyl⟩—Cl, CH₃ |
| 4-Cl | N | CO | —O—C₃H₇ |
| 4-Cl | N | CH(OH) | —O—C₃H₇ |
| 4-Cl | CH | CO | —O—C₃H₇ |
| 4-Cl | CH | CH(OH) | —O—C₃H₇ |
| 4-Cl | N | CO | —O—C(CH₃)₃ |
| 4-Cl | N | CH(OH) | —O—C(CH₃)₃ |
| 4-Cl | CH | CO | —O—C(CH₃)₃ |

TABLE 1-continued

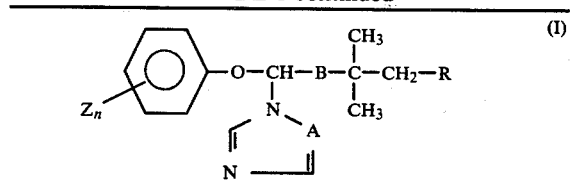

| $Z_n$ | A | B | R |
|---|---|---|---|
| 4-Cl | CH | CH(OH) | —O—C(CH$_3$)$_3$ |
| 2,4-Cl$_2$ | N | CO | —O—CH$_2$—C$_6$H$_4$—Cl |
| 2,4-Cl$_2$ | N | CH(OH) | —O—CH$_2$—C$_6$H$_4$—Cl |
| 2,4-Cl$_2$ | CH | CO | —O—CH$_2$—C$_6$H$_4$—Cl |
| 2,4-Cl$_2$ | CH | CH(OH) | —O—CH$_2$—C$_6$H$_4$—Cl |
| 4-Cl,2-SCH$_3$ | N | CO | —C$_6$H$_4$—Cl |
| 4-Cl,2-SCH$_3$ | CH | CO | —C$_6$H$_4$—Cl |
| 4-Cl,2-SCH$_3$ | N | CH(OH) | —C$_6$H$_4$—Cl |
| 4-Cl,2-SCH$_3$ | CH | CH(OH) | —C$_6$H$_4$—Cl |
| 4-C$_6$H$_4$—Cl | N | CO | —C$_6$H$_4$—CN |
| 4-C$_6$H$_4$—Cl | CH | CO | —C$_6$H$_4$—CN |
| 4-C$_6$H$_4$—Cl | N | CH(OH) | —C$_6$H$_4$—CN |
| 4-C$_6$H$_4$—Cl | CH | CH(OH) | —C$_6$H$_4$—CN |
| 4-C$_6$H$_5$ | N | CO | —OCH$_3$ |
| 4-C$_6$H$_5$ | CH | CO | —OCH$_3$ |
| 4-C$_6$H$_5$ | N | CH(OH) | —OCH$_3$ |
| 4-C$_6$H$_5$ | CH | CH(OH) | —OCH$_3$ |
| 4-Cl | N | CO | —O—C$_6$H$_4$—COOCH$_3$ |
| 4-Cl | CH | CO | —O—C$_6$H$_4$—COOCH$_3$ |
| 4-Cl | N | CH(OH) | —O—C$_6$H$_4$—COOCH$_3$ |
| 4-Cl | CH | CH(OH) | —O—C$_6$H$_4$—COOCH$_3$ |
| 4-Cl | N | CO | —O—C$_6$H$_4$—NO$_2$ |
| 4-Cl | CH | CO | —O—C$_6$H$_4$—NO$_2$ |
| 4-Cl | N | CH(OH) | —O—C$_6$H$_4$—NO$_2$ |
| 4-Cl | CH | CH(OH) | —O—C$_6$H$_4$—NO$_2$ |
| 4-Cl,2-CH$_3$ | N | CO | —O—C$_6$H$_4$—N(CH$_3$)$_2$ |
| 4-Cl,2-CH$_3$ | CH | CO | —O—C$_6$H$_4$—N(CH$_3$)$_2$ |
| 4-Cl,2-CH$_3$ | N | CH(OH) | —O—C$_6$H$_4$—N(CH$_3$)$_2$ |
| 4-Cl,2-CH$_3$ | CH | CH(OH) | —O—C$_6$H$_4$—N(CH$_3$)$_2$ |
| 4-Cl | N | CO | —O—C$_6$H$_4$—C$_6$H$_5$ |
| 4-Cl | CH | CO | —O—C$_6$H$_4$—C$_6$H$_5$ |
| 4-Cl | N | CH(OH) | —O—C$_6$H$_4$—C$_6$H$_5$ |
| 4-Cl | CH | CH(OH) | —O—C$_6$H$_4$—C$_6$H$_5$ |
| 2,4-Cl$_2$ | N | CO | —O—C$_6$H$_4$—OCH$_3$ |
| 2,4-Cl$_2$ | CH | CO | —O—C$_6$H$_4$—OCH$_3$ |
| 2,4-Cl$_2$ | N | CH(OH) | —O—C$_6$H$_4$—OCH$_3$ |
| 2,4-Cl$_2$ | CH | CH(OH) | —O—C$_6$H$_4$—OCH$_3$ |

TABLE 1-continued (I) Structure: Zn-phenyl-O-CH(N=CH-A ring)-B-C(CH3)2-CH2-R

| Zn | A | B | R |
|---|---|---|---|
| 4-NO2 | N | CO | —O—C6H4—NO2 |
| 4-NO2 | CH | CO | —O—C6H4—NO2 |
| 4-NO2 | N | CH(OH) | —O—C6H4—NO2 |
| 4-NO2 | CH | CH(OH) | —O—C6H4—NO2 |
| 2,4-Cl2 | N | CO | —O—C5H11 |
| 2,4-Cl2 | CH | CO | —O—C5H11 |
| 2,4-Cl2 | N | CH(OH) | —O—C5H11 |
| 2,4-Cl2 | CH | CH(OH) | —O—C5H11 |
| 4-SO2CH3 | N | CO | —O—C2H5 |
| 4-SO2CH3 | CH | CO | —O—C2H5 |
| 4-SO2CH3 | N | CH(OH) | —O—C2H5 |
| 4-SO2CH3 | CH | CH(OH) | —O—C2H5 |
| 3-CF3 | N | CO | —OCH3 |
| 3-CF3 | CH | CO | —OCH3 |
| 3-CF3 | N | CH(OH) | —OCH3 |
| 3-CF3 | CH | CH(OH) | —OCH3 |
| 2,4,6-Cl3 | N | CO | —OC2H5 |
| 2,4,6-Cl3 | CH | CO | —OC2H5 |
| 2,4,6-Cl3 | N | CH(OH) | —OC2H5 |
| 2,4,6-Cl3 | CH | CH(OH) | —OC2H5 |
| 4-Cl | N | CO | —SC2H5 |
| 4-Cl | CH | CO | —SC2H5 |
| 4-Cl | N | CO | —SO2C2H5 |
| 4-Cl | CH | CO | —SO2C2H5 |
| 4-Cl | N | CO | —S—CH(CH3)2 |
| 4-Cl | CH | CO | —S—CH(CH3)2 |
| 4-Cl | N | CO | —SO2CH(CH3)2 |
| 4-Cl | CH | CO | —SO2—CH(CH3)2 |
| 4-Cl | N | CO | —SC3H7 |
| 4-Cl | CH | CO | —SC3H7 |
| 4-Cl | N | CO | —SO2—C3H7 |
| 4-Cl | CH | CO | —SO2—C3H7 |
| 4-Cl | N | CO | —S—C4H9 |
| 4-Cl | CH | CO | —S—C4H9 |
| 4-Cl | N | CO | —SO2—C4H9 |
| 4-Cl | CH | CO | —SO2—C4H9 |
| 4-Cl | N | CO | —S—biphenyl |
| 4-Cl | CH | CO | —S—biphenyl |
| 4-Cl | N | CO | —SO2—biphenyl |
| 4-Cl | CH | CO | —SO2—biphenyl |
| 4-Cl | N | CH(OH) | —SC2H5 |
| 4-Cl | CH | CH(OH) | —SC2H5 |
| 4-Cl | N | CH(OH) | —SO2C2H5 |
| 4-Cl | CH | CH(OH) | —SO2C2H5 |
| 4-Cl | N | CH(OH) | —S—CH(CH3)2 |
| 4-Cl | CH | CH(OH) | —S—CH(CH3)2 |
| 4-Cl | N | CH(OH) | —SO2—CH(CH3)2 |
| 4-Cl | CH | CH(OH) | —SO2—CH(CH3)2 |
| 4-Cl | N | CH(OH) | —SC3H7 |
| 4-Cl | CH | CH(OH) | —SC3H7 |
| 4-Cl | N | CH(OH) | —SO2—C3H7 |
| 4-Cl | CH | CH(OH) | —SO2—C3H7 |
| 4-Cl | N | CH(OH) | —S—C4H9 |
| 4-Cl | CH | CH(OH) | —S—C4H9 |
| 4-Cl | N | CH(OH) | —SO2—C4H9 |
| 4-Cl | CH | CH(OH) | —SO2—C4H9 |
| 4-Cl | N | CH(OH) | —S—biphenyl |
| 4-Cl | CH | CH(OH) | —S—biphenyl |
| 4-Cl | N | CH(OH) | —SO2—biphenyl |
| 4-Cl | CH | CH(OH) | —SO2—biphenyl |
| 4-Cl | N | CO | —S—(2,4-Cl2-phenyl) |
| 4-Cl | CH | CO | —S—(2,4-Cl2-phenyl) |
| 4-Cl | N | CO | —S—(2,4-Cl2-phenyl) |
| 4-Cl | CH | CO | —S—(2,4-Cl2-phenyl) |
| 4-Cl | N | CO | —S—(2,6-Cl2-phenyl) |
| 4-Cl | CH | CO | —S—(2,6-Cl2-phenyl) |
| 4-Cl | N | CO | —SO2—(2,6-Cl2-phenyl) |

TABLE 1-continued $$\text{(I)}$$

Structure: Z_n-phenyl-O-CH(N=CH-N-A)-B-C(CH_3)_2-CH_2-R

| $Z_n$ | A | B | R |
|---|---|---|---|
| 4-Cl | CH | CO | —SO$_2$—(2,6-Cl$_2$-phenyl) |
| 4-Cl | N | CH(OH) | —S—(2,4-Cl$_2$-phenyl) |
| 4-Cl | CH | CH(OH) | —S—(2,4-Cl$_2$-phenyl) |
| 4-Cl | N | CH(OH) | —SO$_2$—(2,4-Cl$_2$-phenyl) |
| 4-Cl | CH | CH(OH) | —SO$_2$—(2,4-Cl$_2$-phenyl) |
| 4-Cl | N | CH(OH) | —S—(2,6-Cl$_2$-phenyl) |
| 4-Cl | CH | CH(OH) | —S—(2,6-Cl$_2$-phenyl) |
| 4-Cl | N | CH(OH) | —SO$_2$—(2,6-Cl$_2$-phenyl) |
| 4-Cl | CH | CH(OH) | —SO$_2$—(2,6-Cl$_2$-phenyl) |
| 2,4-Cl$_2$ | N | CO | —S—(4-Cl-phenyl) |
| 2,4-Cl$_3$ | CH | CO | —S—(4-Cl-phenyl) |
| 2,4-Cl$_2$ | N | CO | —SO$_2$—(4-Cl-phenyl) |
| 2,4-Cl$_2$ | CH | CO | —SO$_2$—(4-Cl-phenyl) |
| 2,4-Cl$_2$ | N | CO | —S—(2,4-Cl$_2$-phenyl) |
| 2,4-Cl$_2$ | CH | CO | —S—(2,4-Cl$_2$-phenyl) |
| 2,4-Cl$_2$ | N | CO | —SO$_2$—(2,4-Cl$_2$-phenyl) |
| 2,4-Cl$_2$ | CH | CO | —SO$_2$—(2,4-Cl$_2$-phenyl) |
| 2,4-Cl$_2$ | N | CO | —S—(2,6-Cl$_2$-phenyl) |
| 2,4-Cl$_2$ | CH | CO | —S—(2,6-Cl$_2$-phenyl) |
| 2,4-Cl$_2$ | N | CO | —SO$_2$—(2,6-Cl$_2$-phenyl) |
| 2,4-Cl$_2$ | CH | CO | —SO$_2$—(2,6-Cl$_2$-phenyl) |
| 2,4-Cl$_2$ | N | CH(OH) | —S—(4-Cl-phenyl) |
| 2,4-Cl$_2$ | CH | CH(OH) | —S—(4-Cl-phenyl) |
| 2,4-Cl$_2$ | N | CH(OH) | —SO$_2$—(4-Cl-phenyl) |
| 2,4-Cl$_2$ | CH | CH(OH) | —SO$_2$—(4-Cl-phenyl) |

TABLE 1-continued

Structure (I):
$$Z_n\text{-C}_6H_4\text{-O-CH(N(-N=CH-A=))-B-C(CH}_3)_2\text{-CH}_2\text{-R}$$

| $Z_n$ | A | B | R |
|---|---|---|---|
| 2,4-Cl$_2$ | N | CH(OH) | —S—(3,4-Cl$_2$-C$_6$H$_3$) |
| 2,4-Cl$_2$ | CH | CH(OH) | —S—(3,4-Cl$_2$-C$_6$H$_3$) |
| 2,4-Cl$_2$ | N | CH(OH) | —SO$_2$—(3,4-Cl$_2$-C$_6$H$_3$) |
| 2,4-Cl$_2$ | CH | CH(OH) | —SO$_2$—(3,4-Cl$_2$-C$_6$H$_3$) |
| 2,4-Cl$_2$ | N | CH(OH) | —S—(2,4-Cl$_2$-C$_6$H$_3$) |
| 2,4-Cl$_2$ | CH | CH(OH) | —S—(2,4-Cl$_2$-C$_6$H$_3$) |
| 2,4-Cl$_2$ | N | CH(OH) | —SO$_2$—(2,4-Cl$_2$-C$_6$H$_3$) |
| 2,4-Cl$_2$ | CH | CH(OH) | —SO$_2$—(2,4-Cl$_2$-C$_6$H$_3$) |
| 2,4-Cl$_2$ | N | CO | —S—CH$_2$—(4-Cl-C$_6$H$_4$) |
| 2,4-Cl$_2$ | CH | CO | —S—CH$_2$—(4-Cl-C$_6$H$_4$) |
| 2,4-Cl$_2$ | N | CO | —SO$_2$—CH$_2$—(4-Cl-C$_6$H$_4$) |
| 2,4-Cl$_2$ | CH | CO | —SO$_2$—CH$_2$—(4-Cl-C$_6$H$_4$) |
| 2,4-Cl$_2$ | N | CH(OH) | —S—CH$_2$—(4-Cl-C$_6$H$_4$) |
| 2,4-Cl$_2$ | CH | CH(OH) | —S—CH$_2$—(4-Cl-C$_6$H$_4$) |
| 2,4-Cl$_2$ | N | CH(OH) | —SO$_2$—CH$_2$—(4-Cl-C$_6$H$_4$) |
| 2,4-Cl$_2$ | CH | CH(OH) | —SO$_2$—CH$_2$—(4-Cl-C$_6$H$_4$) |
| 4-Cl | N | CO | —SCH$_3$ |
| 4-Cl | CH | CO | —SCH$_3$ |
| 4-Cl | N | CO | —SO$_2$—CH$_3$ |
| 4-Cl | CH | CO | —SO$_2$—CH$_3$ |
| 4-Cl | N | CH(OH) | —S—CH$_3$ |
| 4-Cl | CH | CH(OH) | —S—CH$_3$ |
| 4-Cl | N | CH(OH) | —SO$_2$—CH$_3$ |
| 4-Cl | CH | CH(OH) | —SO$_2$—CH$_3$ |
| 4-Cl | N | CO | —S—C(CH$_3$)$_3$ |
| 4-Cl | CH | CO | —S—C(CH$_3$)$_3$ |
| 4-Cl | N | CO | —SO$_2$—C(CH$_3$)$_3$ |
| 4-Cl | CH | CO | —SO$_2$—C(CH$_3$)$_3$ |
| 4-Cl | N | CH(OH) | —S—C(CH$_3$)$_3$ |
| 4-Cl | CH | CH(OH) | —S—C(CH$_3$)$_3$ |
| 4-Cl | N | CH(OH) | —SO$_2$—C(CH$_3$)$_3$ |
| 4-Cl | CH | CH(OH) | —SO$_2$—C(CH$_3$)$_3$ |

If, for example, 1,4-bis-(4-chlorophenoxy)-1-bromo-3,3-dimethyl-butan-2-one and 1,2,4-triazole are used as starting substances in process variant (a), the course of the reaction can be represented by the following equation:

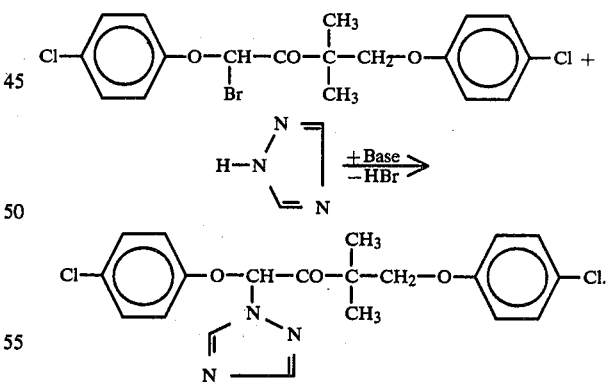

If, for example, 1,4-bis-(4-chlorophenoxy)-3,3-dimethyl-1-(1,2,4-triazol-1-yl)-butan-2-one and sodium borohydride are used as starting substances in process variant (b), the course of the reduction reaction can be represented by the following equation:

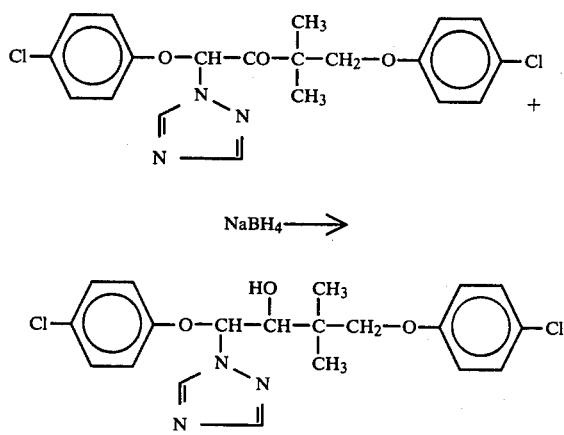

NaBH₄ ⟶

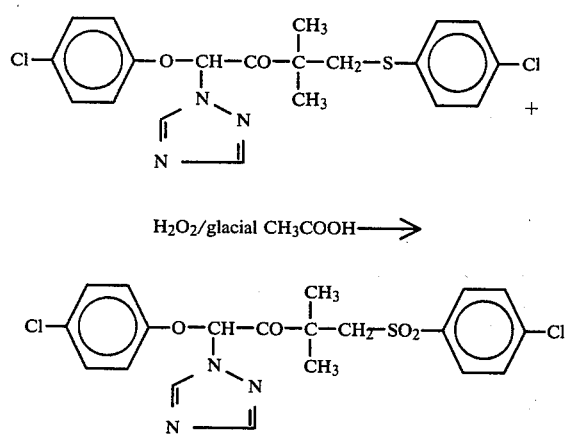

If, for example, 1-(4-chlorophenoxy)-4-(4-chlorophenylmercapto)-3,3-dimethyl-1-(1,2,4-triazol-1-yl)-butan-2-one and hydrogen peroxide in glacial acetic acid are used as starting substances in process variant (c), the course of the oxidation reaction can be represented by the following equation:

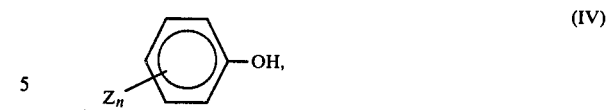

H₂O₂/glacial CH₃COOH ⟶

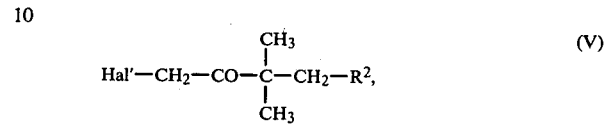

The formula (II) provides a general definition of the halogenoether-ketones to be used as starting substances in carrying out the process according to the invention. In this formula, $R^2$ preferably represents the grouping $X^1$—$R^1$ or cyano. $R^1$ preferably represents straight-chain or branched alkyl with 1 to 6, in particular 1 to 4, carbon atoms or optionally substituted aryl or aralkyl with in each case 6 to 10 carbon atoms in the aryl part and 1 to 2 carbon atoms in the alkyl part, especially phenyl and benzyl, possible substituents being the substituents on aryl which have already been mentioned in the description of the substances of the formula (I).

$X^1$ preferably represents oxygen or sulphur. Z and the index n preferably have those meanings which have already been mentioned as preferred in connection with the description of the substances of the formula (I).

The halogenoether-ketones of the formula (II) have not hitherto been disclosed in the literature. However, they can be obtained by known processes, for example by reacting known phenols of the general formula

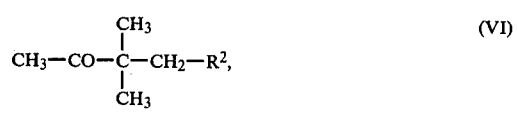

in which Z and n have the abovementioned meanings, with a halogenoether-ketone of the general formula $$Hal'-CH_2-CO-\underset{\underset{CH_3}{|}}{\overset{\overset{CH_3}{|}}{C}}-CH_2-R^2, \quad (V)$$

in which
$R^2$ has the abovementioned meaning and
Hal' represents chlorine or bromine.

The active hydrogen atom which still remains is then replaced by halogen in the customary manner (see also the preparative examples). If appropriate, the halogenoketones of the formula (II) can be further reacted directly, without being isolated.

The halogeno-ketones of the formula (V) likewise have not hitherto been disclosed in the literature. However, they can be obtained by known processes, by reacting 4-substituted 3,3-dimethyl-butan-2-ones of the general formula $$CH_3-CO-\underset{\underset{CH_3}{|}}{\overset{\overset{CH_3}{|}}{C}}-CH_2-R^2, \quad (VI)$$

in which $R^2$ has the abovementioned meaning, with chlorine or bromine in the presence of an inert organic solvent, for example ether or a chlorinated or nonchlorinated hydrocarbon, at room temperature (see also the preparative examples), or with customary chlorinating agents, for example sulphuryl chloride, at 20° to 60° C.

Substituted 3,3-dimethyl-butan-2-ones of the formula (VI) are known (see J. org. Chem. 42, 1709–1717 (1977); J. Am. Chem. Soc. 98, 7882-84 (1976); J. Org. Chem. 37, 2834-2840 (1972) and C.A. 82, 30 898 j (1975)). They can be prepared by reacting butan-2-one derivatives of the general formula $$CH_3-CO-\underset{\underset{CH_3}{|}}{\overset{\overset{CH_3}{|}}{C}}-CH_2-Y, \quad (VII)$$

in which Y represents chlorine, bromine or the grouping —O—SO₂—$R^3$, wherein $R^3$ represents alkyl with 1 to 4 carbon atoms or phenyl which is optionally substituted by alkyl with 1 to 4 carbon atoms, with compounds of the general formula $$M-R^2 \quad (VIII),$$

in which
$R^2$ has the abovementioned meaning and
M represents an alkali metal, preferably sodium or potassium, or hydrogen,
in the presence of an organic solvent, for example glycol or dimethylformamide, and if appropriate in the presence of an acid-binding agent, for example sodium carbonate, at a temperature between 80° and 150° C.

(see also the preparative examples), or by a process in which 3,3-dimethyl-4-hydroxy-butan-2-one, of the formula

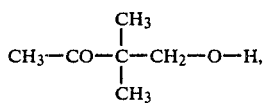

$$CH_3-CO-\underset{\underset{CH_3}{|}}{\overset{\overset{CH_3}{|}}{C}}-CH_2-O-H, \quad (IX)$$

is reacted with compounds of the general formula $$Y'-R^4 \quad (X),$$

in which $R^4$ represents alkyl with 1 to 6, preferably 1 to 4, carbon atoms or optionally substituted benzyl, possible substituents being the substituents mentioned above, and Y' represents chlorine, bromine or the grouping $-O-SO_2-R^5$, wherein $R^5$ represents alkyl or alkoxy with 1 to 4 carbon atoms or phenyl which is optionally substituted by alkyl with 1 to 4 carbon atoms, if appropriate in the presence of water or an organic solvent and if appropriate in the presence of an acid-binding agent, at a temperature between 20° and 100° C.

The butan-2-one derivatives of the formula (VII) are known (see, for example, U.S. Pat. No. 4,255,434 and Journal Org. Chem. 35. 2391 (1970)). They can be obtained in a generally known manner from 3,3-dimethyl-4-hydroxy-butan-2-one (see also the preparative examples).

3,3-Dimethyl-4-hydroxy-butan-2-one of the formula (IX) is likewise known (see, for example, U.S. Pat. No. 4,255,434, supra).

The compounds of the formula (VIII) and (X) are generally known compounds of organic chemistry. If appropriate, the compounds of the formula (VIII) are employed as products prepared in situ.

The formula (III) provides a general definition of the azoles also to be used as starting substances for the process according to the invention.

The azoles of the formula (III) are generally known compounds of organic chemistry.

The formula (Ia) provides a general definition of the keto derivatives to be used as starting substances for the reduction (process variant (b)) which is to be carried out if appropriate. In this formula, A, $R^2$, Z and the index n preferably have those meanings which have already been mentioned as preferred in connection with the description of the substances of the formula (I).

The formula (Ib) provides a general definition of the thio derivatives to be used as starting substances for the oxidation (process variant (c)) which is to be carried out if appropriate. In this formula, $R^1$ preferably represents straight-chain or branched alkyl with 1 to 6 carbon atoms or optionally substituted phenyl or benzyl, preferred possible substituents being the substituents which have already been mentioned above. Z and the index n preferably represent tnose radicals which have already been mentioned as preferred for these substituents in connection with the description of the substances of the formula (I) according to the invention.

The keto derivatives of the formula (Ia) and the thio derivatives of the formula (Ib) are themselves compounds according to the invention; the former may be prepared by process variant (a), the latter by process variant (a) or (b).

Possible diluents for the reaction in process variant (a) are inert organic solvents. These include, as preferences, ketones, such as diethyl ketone and, in particular, acetone and methyl ethyl ketone; nitriles, such as propionitrile, and in particular acetonitrile; alcohols, such as ethanol or isopropanol; ethers, such as tetrahydrofuran or dioxane; benzene; toluene; formamides, such as, in particular, dimethylformamide; and halogenated hydrocarbons.

The reaction in process variant (a) is carried out in the presence of an acid-binding agent. It is possible to add any of the inorganic or organic acid-binding agents which can customarily be used, such as alkali metal carbonates, for example sodium carbonate, potassium carbonate and sodium bicarbonate, or such as lower tertiary alkylamines, cycloalkylamines or aralkylamines, for example triethylamine, N,N-dimethylcyclohexylamine, dicyclohexylamine and N,N-dimethylbenzylamine, and also pyridine and diazabicyclooctane.

Preferably, an appropriate excess of azole is used.

The reaction temperatures can be varied within a substantial range. In general, the reaction is carried out at between about 20° and about 150° C., preferably at from 60° to 120° C. If a solvent is present, it is expedient to carry out the reaction at the boiling point of the particular solvent.

In carrying out the process variant (a), 2 to 4 mols of azole and 1 to 4 mols of acid-binding agent are preferably employed per mole of the compounds of the formula (II). To isolate the compounds of the formula (I), the solvent is distilled off, the residue is taken up in an organic solvent and the mixture is washed with water. The organic phase is dried over sodium sulphate and freed from the solvent in vacuo. The residue is purified by distillation or recrystallization, or salt formation and recrystallization.

The reduction in process variant (b) may be carried out in the customary manner, for example by reaction with a complex hydride, if appropriate in the presence of a diluent, or by reaction with aluminum isopropylate in the presence of a diluent.

If a complex hydride is used, possible diluents for the reaction according to the invention are organic solvents. These include, as preferences, alcohols, such as methanol, ethanol, butanol or isopropanol, and ethers, such as diethyl ether or tetrahydrofuran. The reaction is in general carried out at from 0° to 30° C., preferably at from 0° to 20° C. For this reduction, about 1 mol of a complex hydride, such as sodium hydroxide or lithium alanate, is generally employed per mol of the ketone of the formula (Ia). To isolate the reduced compound of the formula (I), the residue is taken up in dilute hydrochloric acid and the mixture is then rendered alkaline and extracted with an organic solvent. Further working up is effected in the customary manner.

If aluminum isopropylate is used, preferred diluents for the reaction according to the invention are alcohols, such as isopropanol, or inert hydrocarbons, such as benzene. The reaction temperatures can again be varied within a substantial range; in general, the reaction is carried out at between 20° and 120° C., preferably at from 50° to 100° C. To carry out the reaction, about 0.3 to 2 mols of aluminum isopropylate are generally employed per mol of the ketone of the formula (Ia). To isolate the reduced compound of the formula (I), the excess solvent is removed in vacuo and the aluminum compounds formed are decomposed with dilute sulphuric acid or sodium hydroxide solution. Further working up is effected in the customary manner.

The oxidation in process variant (c) may be effected by reaction with customary inorganic or organic oxidizing agents. These include, as preferences, organic peracids, for example peracetic acid, p-nitro-perbenzoic acid and m-chloroperbenzoic acid; inorganic peracids, for example periodic acid; and also hydrogen peroxide in glacial acetic acid or methanol, potassium permanganate and chromic acid.

The reaction temperatures can be varied within a substantial range in carrying out the oxidation. In general, the reaction is carried out at between about $-50°$ and $+100°$ C., preferably between $-30°$ and $80°$ C.

In carrying out the oxidation according to the invention, about 1 to 5 mols of oxidizing agent are generally employed per mol of the compound of the formula (Ib). If 1 mol of oxidizing agent, such as m-chloroperbenzoic acid in methylene chloride or hydrogen peroxide in acetic anhydride, is used at a temperature between $-30°$ and $+30°$ C., the compounds of the formula (I) in which $X=SO$ are preferentially formed. In the case of an excess of oxidizing agent and higher temperatures ($10°$ to $80°$ C.), the compounds of the formula (I) in which $X=SO_2$ are preferentially formed. The oxidation products are isolated in the customary manner.

The following acids can preferably be used for the preparation of physiologically acceptable acid addition salts of the compounds of the formula (I): hydrogen halide acids (for example hydrobromic acid and, in particular, hydrochloric acid), phosphoric acid, nitric acid, sulphuric acid, monofunctional and bifunctional carboxylic acids and hydroxycarboxylic acids (for example acetic acid, maleic acid, succinic acid, fumaric acid, tartaric acid, citric acid, salicylic acid, sorbic acid and lactic acid) and sulphonic acids (for example p-toluenesulphonic acid and 1,5-naphthalenedisulphonic acid). The acid addition salts of the compounds of the formula (I) can be obtained in a simple manner by customary salt formation methods, for example by dissolving a compound of the formula (I) in a suitable inert solvent and adding the acid, for example hydrochloric acid, and they can be isolated in a known manner, for example by filtration, and if appropriate purified by washing with an inert organic solvent.

Salts of metals of main groups II and IV and of subgroups I and II and IV to VIII are preferably used for the preparation of metal salt complexes of the compounds of the formula (I), examples of metals which may be mentioned being copper, zinc, manganese, magnesium, tin, iron and nickel. Preferred anions of the salts are those which are derived from the following acids: hydrogen halide acids (for example hydrochloric acid and hydrobromic acid), phosphoric acid, nitric acid and sulphuric acid.

The metal salt complexes of the compounds of the formula (I) can be obtained in a simple manner by customary processes, for example by dissolving the metal salt in alcohol, for example ethanol, and adding the solution to the compound of the formula (I). The metal salt complexes can be purified in a known manner, for example by filtration, isolation and, if appropriate, by recrystallization.

The active compounds according to the invention exhibit a powerful microbicidal action and can be employed in practice for combating undesired microorganisms. The active compounds are suitable for use as plant protection agents.

Fungicidal agents in plant protection are employed for combating Plasmodiophoromycetes, Oomycetes, Chytridiomycetes, Zygomycetes, Ascomycetes, Basidiomycetes and Deuteromycetes.

The good toleration, by plants, of the active compounds, at the concentrations required for combating plant diseases, permits treatment of above-ground parts of plants, of vegetative propagation stock and seeds, and of the soil.

As plant protection agents, the active compounds according to the invention can be particularly successfully used for combating cereal diseases, such as powdery mildew and rust, Venturia species, such as the apple scab causative organism (*Fusicladium dendriticium*), Uromyces species, such as the bean rust causative organism (*Uromyces phaseoli*), and Erysiphe species, such as the powdery mildew of cucumber causative organism (*Erysiphe cichoracearum*). The active compounds according to the invention also exhibit a generally good in vitro action.

The active compounds can be converted into the customary formulations, such as solutions, emulsions, suspensions, powders, dusting agents, foams, pastes, soluble powders, granules, aerosols, suspension-emulsion concentrates, natural and synthetic materials impregnated with active compound, very fine capsules in polymeric substances, coating compositions for use on seed, and formulations used with burning equipment, such as fumigating cartridges, fumigating cans and fumigating coils, as well as ULV cold mist and warm mist formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.1 to 95 percent by weight of active compound, preferably from 0.5 to 90 percent by weight.

The active compounds according to the invention can be present in the formulations or in the various use forms as a mixture with other active compounds, such as fungicides, bactericides, insecticides, acaricides, nematicides, herbicides, bird repellents, growth factors, plant nutrients and agents for improving soil structure.

The active compounds can be used as such or in the form of their formulations or the use forms prepared therefrom by further dilution, such as ready-to-use solutions, emulsions, suspensions, powders, pastes and granules. They may be used in the customary manner, for example by watering, immersion, spraying, atomizing, misting, vaporizing, injecting, forming a slurry, brushing on, dusting, scattering, dry dressing, moist dressing, wet dressing, slurry dressing or encrusting.

Especially in the treatment of parts of plants, the active compound concentrations in the use forms can be varied within a substantial range. They are, in general, between 1 and 0.0001% by weight, preferably between 0.5 and 0.001%.

In the treatment of seed, amounts of active compound of, in general, 0.001 to 50 g, preferably 0.01 to 10 g, are employed per kilogram of seed.

For the treatment of soil, active compound concentrations of, in general, 0.00001 to 0.1% by weight, preferably 0.0001 to 0.02%, are employed at the place of action.

The present invention also provides a fungicidal composition containing as active ingredient a compound of the present invention in admixture with a solid or liquefied gaseous diluent or carrier or in admixture with a liquid diluent or carrier containing a surface-active agent.

The present invention also provides a method of combating fungi which comprises applying to the fungi, or to a habitat thereof, a compound of the present invention alone or in the form of a composition containing as active ingredient a compound of the present invention in admixture with a diluent or carrier.

The present invention further provides crops protected from damage by fungi by being grown in areas in which immediately prior to and/or during the time of the growing a compound of the present invention was applied alone or in admixture with a diluent or carrier.

It will be seen that the usual methods of providing a harvested crop may be improved by the present invention.

PREPARATIVE EXAMPLES

EXAMPLE 1

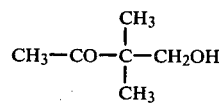

66 g (2.2 mols) of paraformaldehyde and 1 g of potassium hydroxide in 10 ml of methanol were added dropwise to 172 g (2 mols) of methyl isopropyl ketone in 1,000 ml of methanol. The mixture was heated under reflux for 15 hours and the methanol was then distilled off over a column, at an internal temperature of 82° C. The residue was distilled under a waterpump vacuum. 152.7 g (68% of theory) of 2,2-dimethyl-1-hydroxy-butan-3-one of boiling point 80°–82° C./12 mm Hg were obtained.

(b)

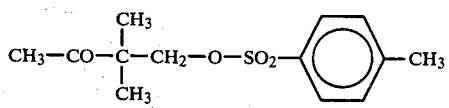

47.6 g (0.25 mol) of 4-toluenesulphonyl chloride were dissolved in 100 ml of chloroform, 35 g (0.3 mol) of 2,2-dimethyl-1-hydroxy-butan-3-one were added, and 40 ml (0.5 mol) of pyridine were added dropwise at 0° to 5° C. The reaction mixture was subsequently stirred at room temperature for 15 hours and poured onto 200 g of ice and 70 ml of concentrated hydrochloric acid and the organic phase was separated off, washed three times with 200 ml of water each time, dried over sodium sulphate and concentrated. The residue was taken up in 100 ml of petroleum ether, whereupon the end product crystallized out. 48 g (71% of theory) of 2,2-dimethyl-1-tosyloxy-butan-3-one were obtained as colorless crystals of melting point 49°–52° C.

(c)

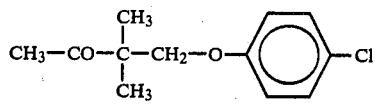

29.7 g (0.55 mol) of sodium methylate were dissolved in 500 ml of methanol, and 70.4 g (0.55 mol) of 4-chlorophenol were added, while stirring. Afteer stirring the mixture for 10 minutes, the solvent was distilled off under reduced pressure and the residue was taken up in 100 ml of glycol. This solution was added to a solution of 135 g (0.5 mol) of 2,2-dimethyl-1-tosyloxy-butan-3-one in 200 ml of glycol. The mixture was stirred at 100° to 120° C. for 48 hours and cooled and the reaction mixture was stirred into 2,000 ml of water. The mixture was extracted twice with 250 ml of diethyl ether each time and the combined organic phases were washed three times with 100 ml of water each time, once with 100 ml of 10% strength sodium hydroxide solution and once more with 100 ml of water, dried over sodium sulphate and distilled. 62.9 g (55.7% of theory) of 1-(4-chlorophenoxy)-2,2-dimethyl-butan-3-one of boiling point 135°–140° C./0.4 mm Hg were obtained.

(d)

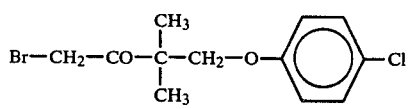

36 g (0.159 mol) of 1-(4-chlorophenoxy)-2,2-dimethyl-butan-3-one were dissolved in 300 ml of chloroform, and 25.5 g (0.159 mol) of bromine were added dropwise at 20° C. in a manner such that continuous decolorization occurred. After the addition, the mixture was stirred at room temperature for 30 minutes and was then concentrated by distilling off the solvent in vacuo. 48.5 g (quantitative conversion) of crude 1-bromo-4-(4-chlorophenoxy)-3,3-dimethyl-butan-2-one were obtained as an oil.

(e)

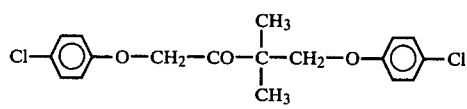

20.6 g (0.16 mol) of 4-chlorophenol and 28 g (0.2 mol) of potassium carbonate were dissolved in 250 ml of acetone. 48.5 g of 1-bromo-4-(4-chlorophenoxy)-3,3-dimethyl-butan-2-one in 50 ml of acetone were slowly added dropwise, under reflux. After the addition, the mixture was stirred under reflux for 15 hours and filtered and the filtrate was concentrated. The residue was taken up in 500 ml of methylene chloride and the mixture was extracted by shaking with 200 ml of water, 200 ml of saturated sodium bicarbonate solution and again with 200 ml of water.

The organic phase was dried over sodium sulphate and concentrated and the residue was taken up in 150 ml of diisopropyl ether. After concentrating the mixture, 36.6 g (65% of theory) of 1,4-bis-(4-chlorophenoxy)-3,3-dimethyl-butan-2-one were obtained as colorless crystals of melting point 76°–77° C.

(f)

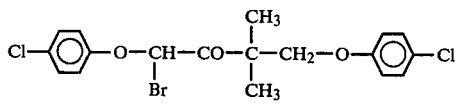

36.6 g (0.1 mol) of 1,4-bis-(4-chlorophenoxy)-3,3-dimethyl-butan-2-one were dissolved in 250 ml of chloroform, and 16.6 g (0.1 mol) of bromine were added dropwise at 20° C. in a manner such that continuous decolorization occurred. After the addition, the mixture was subsequently stirred at room temperature for 30 minutes and was then concentrated by distilling off the solvent in vacuo. 43.2 g (quantitative conversion) of 1,4-bis-(4-chlorophenoxy)-1-bromo-3,3-dimethyl-butan-2-one were obtained as an oil, which was further reacted directly.

(g)

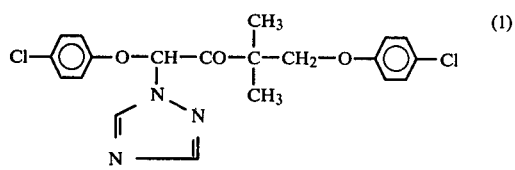

21.6 g (0.05 mol) of crude 1,4-bis-(4-chlorophenoxy)-1-bromo-3,3-dimethyl-butan-2-one were stirred under reflux with 14 g (0.2 mol) of 1,2,4-triazole in 100 ml of acetonitrile for 17 hours. The mixture was then concentrated by distilling off the solvent under reduced pressure. The residue was taken up in 400 ml of methylene chloride and the mixture was extracted by shaking three times with 800 ml of water each time, dried over sodium sulphate and concentrated. The residue was taken up in 100 ml of acetone, and 9 g (0.05 mol) of 1,5-naphthalenedisulphonic acid tetrahydrate in 50 ml of acetone were added dropwise. The precipitate formed was filtered off and suspended in 200 ml of methylene chloride. 400 ml of saturated sodium bicarbonate solution were added, the mixture was stirred for 30 minutes and the organic phase was separated off, dried over sodium sulphate and concentrated by distilling off the solvent. 12.3 g (58.6% of theory) of 1,4-bis-(4-chlorophenoxy)-3,3-dimethyl-1-(1,2,4-triazol-1-yl)-butan-2-one were obtained as an oil.

The corresponding 1,5-naphthalenedisulphonate salt had a melting point of 206°–208° C.

EXAMPLE 2

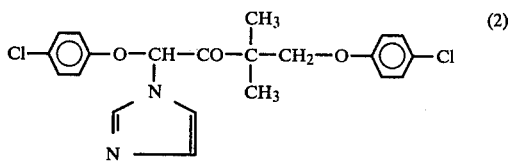

21.6 g (0.05 mol) of crude 1,4-bis-(4-chlorophenoxy)-1-bromo-3,3-dimethyl-butan-2-one were stirred under reflux with 14 g (0.2 mol) of imidazole in 100 ml of acetonitrile for 17 hours. The mixture was then concentrated by distilling off the solvent under reduced pressure. The residue was taken up in 400 ml of methylene chloride and the mixture was extracted by shaking three times with 800 ml of water each time, dried over sodium sulphate and concentrated. The residue was taken up in 100 ml of acetone and 9 g (0.05 mol) of 1,5-naphthalenedisulphonic acid tetrahydrate in 50 ml of acetone were added dropwise. The precipitate formed was filtered off and suspended in 200 ml of methylene chloride. 400 ml of saturated sodium bicarbonate solution were added, the mixture was stirred for 30 minutes and the organic phase was separated off. After distilling off the solvent, 14.1 g (67% of theory) of 1,4-bis-(4-chlorophenoxy)-3,3-dimethyl-1-(imidazol-1-yl)-butan-2-one were obtained as an oil.

The corresponding 1,5-naphthalenedisulphonate salt had a melting point of 214°–217° C.

EXAMPLE 3

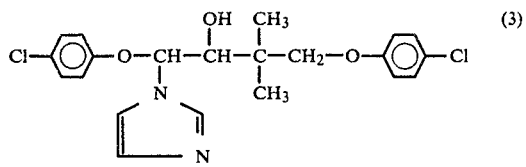

13.1 g (0.031 mol) of 1,4-bis-(4-chlorophenoxy)-3,3-dimethyl-1-(imidazol-1-yl)-butan-2-one (Example 2) were dissolved in 100 ml of methanol, and 1.4 g of sodium borohydride were added in portions at 0° to 5° C. The mixture was subsequently stirred at room temperature for 5 hours, acidified with 10 ml of 2 N hydrochloric acid and stirred at room temperature for a further 2 hours. The solvent was then distilled off in vacuo and the residue was taken up in 300 ml of methylene chloride. The mixture was stirred with 200 ml of saturated sodium bicarbonate solution, the organic phase was separated off, washed twice with 300 ml of water each time and dried over sodium sulphate and the solvent was distilled off in vacuo. The colorless residue was taken up in 50 ml of diisopropyl ether and the crystals formed were filtered off. 10.8 g (82.7% of theory) of 1,4-bis-(4-chlorophenoxy)-3,3-dimethyl-1-(imidazol-1-yl)-butan-2-ol were obtained as a diastereomer mixture of melting point 142°–144° C.

EXAMPLE 4

(a) (i)

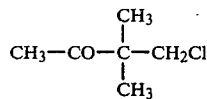

11.6 g (0.1 mol) of 2,2-dimethyl-1-hydroxy-butan-3-one (for the preparation, see Example 1a) were added dropwise to 20.5 g (0.1 mol) of N,N-diethyl-1,2,2-trichlorovinyl-amine at 50° to 60° C. (cooling with ice). After stirring the mixture at 60° C. for two hours, it was distilled under a waterpump vacuum. 8.1 g (60% of theory) of 1-chloro-2,2-dimethyl-butan-3-one, i.e. 4-chloropinacolin, of boiling point 60°–62° C./12 mm Hg were obtained.

(ii) (1-Chloro-2,2-dimethyl-butan-3-one was obtained in a yield of 70% when equimolar amounts of 2,2-dimethyl-1-hydroxy-butan-3-one and triphenylphosphine were heated under reflux in ten times the amount of carbon tetrachloride for 12 hours, the solvent was distilled off, the residue was taken up in ether, the mixture was filtered and the filtrate was distilled.)

(b)

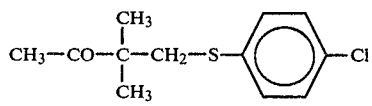

134.5 g (1 mol) of 4-chloropinacolin were stirred with 216.7 g (1.5 mol) of 4-chlorothiophenol and 210 g (1.52 mol) of potassium carbonate in 500 ml of dimethylformamide at 150° C. for 15 hours. The mixture was allowed to cool to room temperature and was stirred with 10 liters of water and extracted with ether. The ether phase was dried over sodium sulphate and concentrated and the residue was distilled in vacuo. 189 g (78% of theory) of 1-(4-chlorophenylmercapto)-2,2-dimethyl-butan-3-one of boiling point 146° C./0.5 mm Hg were obtained.

(c)

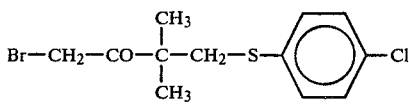

97 g (0.4 mol) of 1-(4-chlorophenylmercapto)-2,2-dimethyl-butan-3-one were dissolved in 400 ml of carbon tetrachloride, and 64 g (0.4 mol) of bromine were added dropwise in the course of 30 minutes. The mixture was subsequently stirred at room temperature for 1 hour and was then concentrated by distilling off the solvent. 127 g (99% of theory) of crude 1-bromo-4-(4-chlorophenylmercapto)-3,3-dimethyl-butan-2-one were obtained as a yellowish oil, which was further reacted directly.

(d)

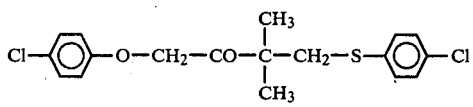

133.7 g (0.41 mol) of 1-bromo-4-(4-chlorophenylmercapto)-3,3-dimethyl-butan-2-one were heated to 100° C. with 64 g (0.5 mol) of 4-chlorophenol and 69 g (0.5 mol) of potassium carbonate in 500 ml of toluene for 5 hours. The mixture was then allowed to cool and was filtered. The filtrate was extracted by shaking with dilute sodium hydroxide solution, rinsed with water, dried over sodium sulphate and concentrated by distilling off the solvent in vacuo. 110.5 g (72% of theory) of 1-(4-chlorophenoxy)-4-(4-chlorophenylmercapto)-3,3-dimethyl-butan-2-one were obtained as a yellowish oil with a refractive index $n_D^{20}$ of 1.5932.

(e)

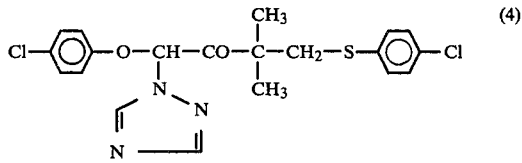

48 g (0.3 mol) of bromine were added dropwise to 110.5 g (0.3 mol) of 1-(4-chlorophenoxy)-4-(4-chlorophenylmercapto)-3,3-dimethyl-butan-2-one in 750 ml of carbon tetrachloride at room temperature. The mixture was subsequently stirred at room temperature for one hour and was concentrated by distilling off the solvent in vacuo, and the residue was taken up in 750 ml of toluene. 73 g (1.06 mol) of 1,2,4-triazole and 150 g (1.06 mol) of potassium carbonate were added to this solution. The mixture was heated to 90° C. for 8 hours and allowed to cool to room temperature and the organic phase was separated off. This phase was extracted with dilute sodium hydroxide solution, rinsed with water, dried over sodium sulphate and concentrated in vacuo.

34 g (26% of theory) of 1-(4-chlorophenoxy)-4-(4-chlorophenylmercapto)-3,3-dimethyl-1-(1,2,4-triazol-1-yl)-butan-2-one of melting point 115° C. were obtained.

EXAMPLE 5

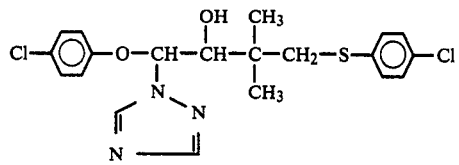
(5)

0.35 g (0.0092 mol) of sodium borohydride in 8 ml of water was added in portions to 10 g (0.023 mol) of 1-(4-chlorophenoxy)-4-(4-chlorophenylmercapto)-3,3-dimethyl-1-(1,2,4-triazol-1-yl)-butan-2-one (Example 4e) in 200 ml of methanol. The reaction mixture was subsequently stirred at 20° C. for 4 hours, poured onto water and extracted with ether. The ether phase was dried over sodium sulphate and concentrated. 5.5 g (54.6% of theory) of 1-(4-chlorophenoxy)-4-(4-chlorophenylmercapto)-3,3-dimethyl-1-(1,2,4-triazol-1-yl)-butan-2-ol of melting point 132° C. were obtained.

EXAMPLE 6

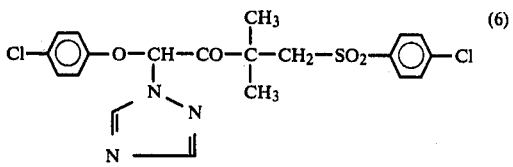
(6)

10 g (0.023 mol) of 1-(4-chlorophenoxy)-4-(4-chlorophenylmercapto)-3,3-dimethyl-1-(1,2,4-triazol-1-yl)-butan-2-one (Example 4e) in 70 ml of glacial acetic acid were stirred with 14.2 g (0.125 mol) of 30% strength hydrogen peroxide at 50° C. for 5 hours. The reaction mixture was then poured into 250 ml of water and extracted with ether. The ether phase was extracted by shaking with sodium bicarbonate solution and was rinsed with water, dried over sodium sulphate and concentrated. 8.4 g (74% of theory) of 1-(4-chlorophenoxy)-4-(4-chlorophenylsulphonyl)-3,3-dimethyl-1-(1,2,4-triazol-1-yl)-butan-2-one of melting point 55°–60° C. were obtained.

The following compounds of the general formula

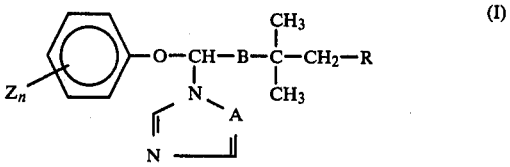
(I)

were obtained in a manner analogous to that described in one of Examples 1 to 6:

TABLE 2

| Compound No. | $Z_n$ | A | B | R | Melting point (°C.) or refractive index |
|---|---|---|---|---|---|
| 7 | 2,4-$Cl_2$ | N | CO | —O—C$_6$H$_4$—Cl | 212 (xHCl) |
| 8 | 2,4-$Cl_2$ | N | CO | —O—C$_6$H$_3$Cl$_2$ | 140–42 (xHCl) |
| 9 | 4-Cl | N | CO | —O—C$_6$H$_3$Cl$_2$ | 40 |
| 10 | 4-Cl | N | CO | —O—$C_2H_5$ | 67–68 |
| 11 | 4-Cl | N | CO | —O—$CH_3$ | Oil |
| 12 | 4-Cl | N | CH(OH) | —O—C$_6$H$_4$—Cl | 105 |
| 13 | 4-Cl | N | CH(OH) | —O—C$_6$H$_5$ | 110–11 |
| 14 | 2,4-$Cl_2$ | N | CH(OH) | —O—C$_6$H$_4$—Cl | 165 (decomposition) (xHCl) |
| 15 | 2,4-$Cl_2$ | N | CH(OH) | —O—C$_6$H$_3$Cl$_2$ | 132 |

TABLE 2-continued

| Compound No. | $Z_n$ | A | B | R | Melting point (°C.) or refractive index |
|---|---|---|---|---|---|
| 16 | 2,4-Cl$_2$ | N | CH(OH) | —O—C$_6$H$_4$—Br | 147 (xHCl) |
| 17 | 4-Cl | N | CH(OH) | —O—(2,6-Cl$_2$C$_6$H$_3$) | 128–30 |
| 18 | 2,4-Cl$_2$ | CH | CO | —O—C$_6$H$_4$—Cl | 134–40 (decomposition) (xHCl) |
| 19 | 2,4-Cl$_2$ | CH | CO | —O—(3,4-Cl$_2$C$_6$H$_3$) | 167–75 (xHCl) |
| 20 | 4-Cl | CH | CO | —O—(2,6-Cl$_2$C$_6$H$_3$) | 115 (decomposition) (xHCl) |
| 21 | 2,4-Cl$_2$ | CH | CH(OH) | —O—(3,4-Cl$_2$C$_6$H$_3$) | 118 |
| 22 | 4-Cl | CH | CH(OH) | —O—(2,6-Cl$_2$C$_6$H$_3$) | 172 |
| 23 | 4-Cl | N | CO | —S—C$_6$H$_5$ | 75–78 |
| 24 | 4-Cl | N | CO | —SO$_2$—C$_6$H$_5$ | 25–30 |
| 25 | 4-Cl | N | CH(OH) | —S—C$_6$H$_5$ | 22–25 |
| 26 | 4-Cl | N | CH(OH) | —SO$_2$—C$_6$H$_4$—Cl | 77–80 |
| 27 | 4-Cl | CH | CO | —S—C$_6$H$_4$—Cl | $n_D^{20}$ = 1.5838 |
| 28 | 4-Cl | CH | CH(OH) | —S—C$_6$H$_4$—Cl | 114–16 |
| 29 | 4-Cl | CH | CO | —SO$_2$—C$_6$H$_4$—Cl | 134–38 |
| 30 | 4-Cl | CH | CH(OH) | —OCH$_3$ | 112–20 |
| 31 | 2,4-Cl | CH | CO | —O—C$_6$H$_4$—Br | 108–10 (xHCl) (decomposition) |
| 32 | 2,4-Cl$_2$ | CH | CH(OH) | —O—C$_6$H$_4$—Br | 120–23 |

TABLE 2-continued

| Compound No. | $Z_n$ | A | B | R | Melting point (°C.) or refractive index |
|---|---|---|---|---|---|
| 33 | 4-Cl | CH | CH(OH) | —SO₂—C₆H₄—Cl | 176-83 |
| 34 | 2,4-Cl₂ | CH | CH(OH) | —S—C₆H₄—Cl | 132 |
| 35 | 2,4-Cl₂ | N | CO | —O—C₆H₄—Br | 30 |
| 36 | 2,4-Cl₂ | CH | CO | —S—C₆H₄—Cl | oil |
| 37 | 4-F | CH | CO | —S—C₆H₄—Cl | oil |
| 38 | 4-F | CH | CH(OH) | —S—C₆H₄—Cl | 25 |
| 39 | 4-F | CH | CO | —S—C₆H₅ | $n_D^{20} = 1.5542$ |
| 40 | 4-F | CH | CH(OH) | —S—C₆H₅ | 48-50 |
| 41 | 4-C₆H₅ | CH | CO | —S—C₆H₅ | viscous oil |
| 42 | 4-C₆H₅ | CH | CH(OH) | —S—C₆H₄—Cl | 78 |
| 43 | 4-C₆H₅ | CH | CH(OH) | —S—C₆H₅ | 60 |
| 44 | 4-C₆H₅ | CH | CO | —S—C₆H₄—Cl | viscous oil |
| 45 | 4-F | CH | CO | —S—C₆H₄—F | $n_D^{20} = 1.5564$ |
| 46 | 4-Cl | CH | CO | —S—C₆H₄—F | $n_D^{20} = 1.5585$ |
| 47 | 4-C₆H₅ | CH | CO | —S—C₆H₄—F | viscous oil |
| 48 | 4-F | CH | CH(OH) | —S—C₆H₄—F | 10 |
| 49 | 4-C₆H₅ | CH | CH(OH) | —S—C₆H₄—F | 80 |
| 50 | 4-Cl | CH | CH(OH) | —S—C₆H₄—F | 20 |

EXAMPLES OF USE

The fungicidal activity of the compounds of this invention is illustrated by the following examples wherein the compounds according to the present invention are each identified by the number (given in brackets) from the preparative examples and table hereinabove.

The known comparison compounds are identified as follows:

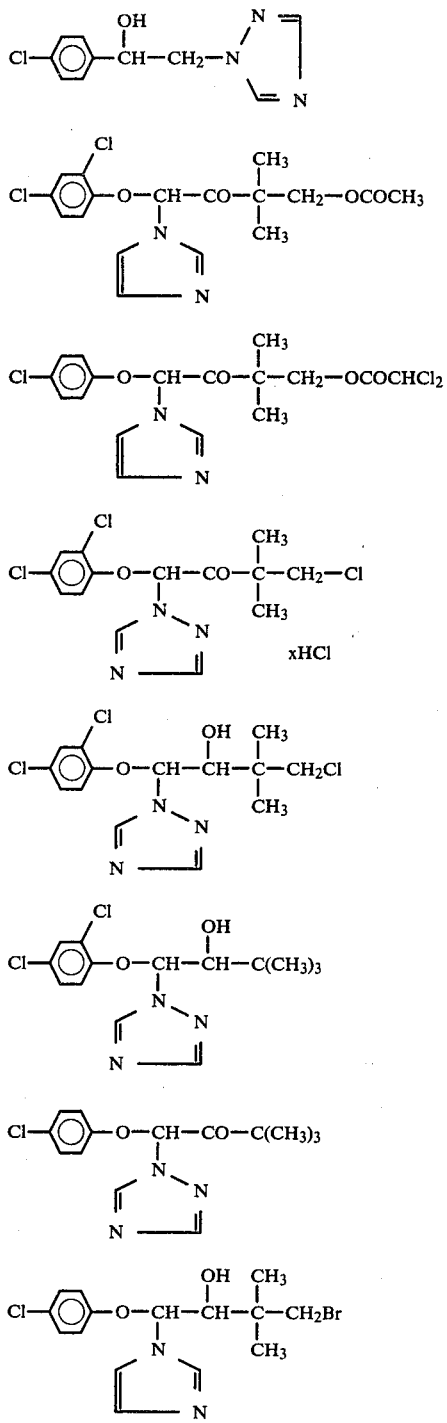

EXAMPLE 7

Erysiphe test (barley)/protective
Solvent: 100 parts by weight of dimethylformamide
Emulsifier: 0.25 part by weight of alkylaryl polyglycol ether To produce a suitable preparation of active compound, 1 part by weight of active compound was mixed with the stated amounts of solvent and emulsifier, and the concentrate was diluted with water to the desired concentration.

To test for protective activity, young plants were sprayed with the preparation of active compound until dew-moist. After the spray coating had dried on, the plants were dusted with spores of *Erysiphe graminis f. sp. hordei*.

The plants were placed in a greenhouse at a temperature of about 20° C. and a relative atmospheric humidity of about 80%, in order to promote the development of powdery mildew pustules.

Evaluation was carried out 7 days after the inoculation.

In this test, a significantly superior activity, compared with the compounds (A) and (B) known from the prior art was shown, for example, by compounds (2), (18), (19), (22), (12), (13), (1), (14), (7), (8) and (9). Test results are given in the following table.

TABLE 3

Erysiphe test (barley)/Protective

| Active compound | Active compound concentration in the spray liquor in % by weight | Disease infection in % of the untreated control |
|---|---|---|
| (B) | 0.025 | 50.0 |
| (A) | 0.025 | 100 |
| (2) | 0.025 | 16.3 |
| (18) | 0.025 | 11.3 |
| (19) (HCl salt) | 0.025 | 3.8 |
| (22) | 0.025 | 0.0 |
| (12) | 0.025 | 33.8 |
| (13) | 0.025 | 8.8 |
| (1) | 0.025 | 11.3 |
| (14) (HCl salt) | 0.025 | 16.3 |
| (7) (HCl salt) | 0.025 | 3.8 |
| (8) (HCl salt) | 0.025 | 7.5 |
| (9) | 0.025 | 0.0 |

EXAMPLE 8

Uromyces test (dwarf beans)/protective
Solvent: 4.7 parts by weight of acetone
Emulsifier: 0.3 part by weight of alkylaryl polyglycol ether
Water: 95.0 parts by weight The amount of the active compound required for the desired concentration of the active compound in the spray liquid was mixed with the stated amount of solvent, and the concentrate was diluted with the stated amount of water which contained the stated addition.

Young bean plants in the 2-leaf stage were sprayed with the spray liquid until dripping wet. The plants remained in a greenhouse for 24 hours at 20°-22° C. and at a relative atmospheric humidity of 70% in order to dry. They were then inoculated with an aqueous uredospore suspension of the bean rust causative organism (*Uromyces phaseoli*) and incubated for 24 hours in a dark humidity chamber at 20°-22° C. and 100% relative atmospheric humidity.

The plants were then set up in a greenhouse under intensive illumination for 9 days at 20°-22° C. and at a relative atmospheric humidity of 70-80%.

10 days after the inoculation, the infection of the plants was determined. The assessment data were converted to percent infection. 0% denoted no infection and 100% denoted that the plants are completely infected.

In this test, a significantly superior activity, compared with the compounds (E), (F) and (G) known from the prior art, was shown, for example by the compounds (12), (1), (14), (7), (8), (15) and (9). Test results are shown in the following table.

TABLE 4

Uromyces test/protective

| Active compound | Infection in % at an active compound concentration of: 0.001% |
|---|---|
| (E) | 71 |
| (F) | 75 |
| (G) | 62 |
| (12) | 10 |
| (1) | 0 |
| (14) (HCl salt) | 29 |
| (7) (HCL salt) | 29 |
| (8) (HCl salt) | 50 |
| (15) | 50 |
| (9) | 21 |

EXAMPLE 9

Fusicladium test (apple)/protective
Solvent: 4.7 parts by weight of acetone
Emulsifier: 0.3 part by weight of alkylaryl polyglycol ether
Water: 95.0 parts by weight The amount of active compound required for the desired concentration of the active compound in the spray liquid was mixed with the stated amount of solvent, and the concentrate was diluted with the stated amount of water which contained the stated addition.

Young apple seedlings in the 4 to 6 leaf stage were sprayed with the spray liquid until dripping wet. The plants remained in a greenhouse for 24 hours at 20° C. and at a relative atmospheric humidity of 70%. They were then inoculated with an aqueous conidium suspension of the apple scab causative organism (*Fusicladium dendriticum*) and incubated for 18 hours in a humidity chamber at 18° to 20° C. and at a relative atmospheric humidity of 100%.

The plants were then again brought into a greenhouse for 14 days.

15 days after inoculation, the infection of the seedlings was determined. The assessment data were converted to percent infection. 0% denoted no infection and 100% denoted that the plants were totally infected.

In this test, a significantly superior activity, compared with the compound (D) known from the prior art, was shown, for example, by the compounds (12) and (13).

TABLE 5

Fusicladium test (apple)/protective

| Active compound | Infection in % at an active compound concentration of 0.0005% |
|---|---|
| (D) | 15 |
| (12) | 10 |
| (13) | 4 |

EXAMPLE 10

Erysiphe test (cucumbers)/protective
Solvent: 4.7 parts by weight of acetone
Emulsifier: 0.3 part by weight of alkylaryl polyglycol ether
Water: 95.0 parts by weight The amount of the active compound required for the desired concentration of active compound in the spray liquid was mixed with the stated amount of solvent and the concentration was diluted with the stated amount of water which contained the stated addition.

Young cucumber plants with about three foliage leaves were sprayed with the spray liquid until dripping wet. The cucumber plants remained in a greenhouse for 24 hours to dry. They were then, for the purpose of inoculation, dusted with conidia of the fungus *Erysiphe cichoracearum*. The plants were subsequently placed in a greenhouse at 23° to 24° C. and at a relative atmospheric humidity of about 75%.

After 12 days, the infection of the cucumber plants was determined. The assessment data were converted to percent infection. 0% denoted no infection and 100% denoted that the plants were totally infected.

In this test, a significantly superior activity, compared with the compounds (C) and (H) known from the prior art, was shown, for example by the compounds (2), (18), (20) and (22).

TABLE 6

Erysiphe test (cucumbers)/protective

| Active compound | Infection in % at an active compound concentration of 0.0005% |
|---|---|
| (H) | 75 |
| (C) | 100 |
| (2) | 12 |
| (18) (HCl salt) | 19 |
| (20) (HCl salt) | 19 |
| (22) | 50 |

It will be understood that the specification and examples are illustrative but not limitative of the present invention and that other embodiments within the spirit and scope of the invention will suggest themselves to those skilled in the art.

We claim:

1. A 4-substituted 1-azolyl-1-phenoxy-3,3-dimethyl-butan-2-one or -ol of the formula $$Z_n\text{-}C_6H_4\text{-}O\text{-}CH\text{-}B\text{-}\underset{CH_3}{\underset{|}{C}}\text{-}CH_2\text{-}R$$

with the $CH$ group bearing an azolyl substituent (N-A=N ring)

in which
A is a nitrogen atom or CH,
B is —CO— or CH(OH),
R is X—R$^1$,
R$^1$ is optionally substituted phenyl or naphthyl or optionally substituted phenylalkyl or naphthylalkyl with 1 to 2 carbon atoms in the alkyl part, each substituent being selected from halogen, cyano, nitro, alkoxycarbonyl with 1 to 4 carbon atoms in the alkyl part, alkyl or alkoxy with 1 to 4 carbon atoms, dialkylamino with 1 to 2 carbon atoms in each alkyl part and phenyl optionally substituted by halogen,
X is oxygen, sulphur, SO or SO$_2$,
Z each independently is halogen, alkyl or alkoxy with 1 to 4 carbon atoms, halogenalkyl with 1 to 2 carbon atoms and 1 to 5 halogen atoms, alkylthio with 1 to 4 carbon atoms, alkylsulphonyl with 1 to 4 carbon atoms, nitro, cyano, alkoxycarbonyl with 1 to 4 carbon atoms in the alkyl part or phenyl optionally substituted by halogen, and n is 0, 1, 2 or 3, or an addition product thereof with a physiologically acceptable acid or with a metal salt.

2. A compound according to claim 1, in which
$R^1$ is optionally substituted phenyl or benzyl, each substituent being selected from fluorine, chlorine, bromine, cyano, nitro, methoxycarbonyl, methyl, ethyl, isopropyl, tert.-butyl, methoxy, dimethylamino, phenyl and phenyl substituted by fluorine or chlorine.

Z is fluorine, chlorine, bromine, iodine, methyl, ethyl, isopropyl, tert.-butyl, methoxy, nitro, cyano, methoxycarbonyl, ethoxycarbonyl, methylthio, methylsulphonyl, trifluoromethyl or phenyl which is optionally substituted by fluorine or chlorine, and n represents 0, 1 or 2, or an addition product thereof with a hydrogen halide acid, phosphoric acid, sulphuric acid, nitric acid, a sulphonic acid or a monofunctional or bifunctional carboxylic or hydroxycarboxylic acid, or with a metal salt, the metal of which is copper, zinc, manganese, magnesium, tin, iron or nickel and the anion of which is halide, sulphate, nitrate or phosphate.

3. A compound according to claim 1, wherein such compound is 1,4-bis-(4-chlorophenoxy)-3,3-dimethyl-1-(1,2,4-triazol-1-yl)-butan-2-one of the formula

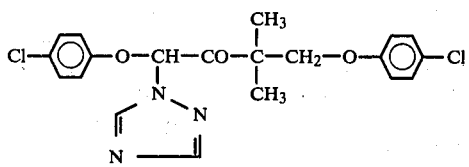

or an addition product thereof with a physiologically acceptable acid or with a metal salt.

4. A compound according to claim 1, wherein such compound is 1-(4-chlorophenoxy)-4-(3,4-dichlorophenoxy)-3,3-dimethyl-1-(1,2,4-triazol-1-yl)-butan-2-one of the formula

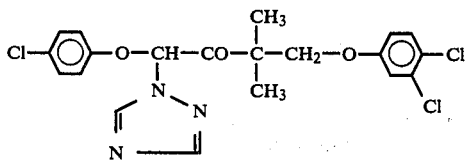

or an addition product thereof with a physiologically acceptable acid or with a metal salt.

5. A compound according to claim 1, wherein such compound is 1-(4-chlorophenoxy)-4-phenoxy-3,3-dimethyl-1-(1,2,4-triazol-1-yl)-butan-2-ol of the formula

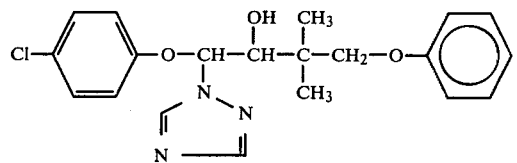

or an addition product thereof with a physiologically acceptable acid or with a metal salt.

6. A compound according to claim 1, wherein such compound is 1-(4-chlorophenoxy)-4-(2,6-dichlorophenoxy)-3,3-dimethyl-1-(1,2,4-triazol-1-yl)-butan-2-ol of the formula

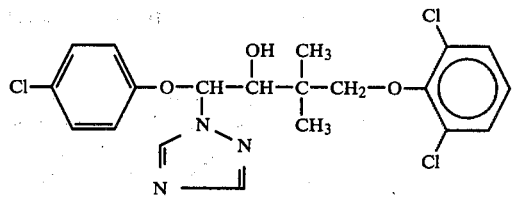

or an addition product thereof with a physiologically acceptable acid or with a metal salt.

7. A fungicidal composition comprising a fungicidally effective amount of a compound or addition product according to claim 1 in admixture with a diluent.

8. A method of combating fungi comprising applying to the fungi, or to a habitat thereof, a fungicidally effective amount of a compound or addition product according to claim 1.

9. The method according to claim 8, wherein such compound is
1,4-bis-(4-chlorophenoxy)-3,3-dimethyl-1-(1,2,4-triazol-1-yl)-butan-2-one,
1-(4-chlorophenoxy)-4-(3,4-dichlorophenoxy)-3,3-dimethyl-1-(1,2,4-triazol-1-yl)-butan-2-one,
1-(4-chlorophenoxy)-4-phenoxy-3,3-dimethyl-1-(1,2,4-triazol-1-yl)-butan-2-ol or
1-(4-chlorophenoxy)-4-(2,6-dichlorophenoxy)-3,3-dimethyl-1-(1,2,4-triazol-1-yl)-butan-2-ol or an addition product thereof with a physiologically acceptable acid or with a metal salt.

* * * * *